US010457772B2

(12) United States Patent
Boday et al.

(10) Patent No.: US 10,457,772 B2
(45) Date of Patent: Oct. 29, 2019

(54) PREPARATION OF ROBUST POLYTHIOAMINAL CARRIERS

(71) Applicants: International Business Machines Corporation, Armonk, NY (US); AGENCY FOR SCIENCE, TECHNOLOGY AND RESEARCH (ASTAR), Singapore (SG)

(72) Inventors: Dylan J. Boday, Tucson, AZ (US); Willy Chin, Singapore (SG); Jeannette M. Garcia, San Leandro, CA (US); James L. Hedrick, Pleasanton, CA (US); Eunice Leong Jiayu, Singapore (SG); Shrinivas Venkataraman, Singapore (SG); Zhi Xiang Voo, Singapore (SG); Rudy J. Wojtecki, San Jose, CA (US); Yi Yan Yang, Singapore (SG)

(73) Assignee: International Business Machines Corporation, Armonk, NY (US)

( * ) Notice: Subject to any disclaimer, the term of this patent is extended or adjusted under 35 U.S.C. 154(b) by 116 days.

(21) Appl. No.: 15/699,416

(22) Filed: Sep. 8, 2017

(65) Prior Publication Data
US 2019/0077909 A1    Mar. 14, 2019

(51) Int. Cl.
*C08G 64/00* (2006.01)
*C08G 64/18* (2006.01)
(Continued)

(52) U.S. Cl.
CPC ............ *C08G 64/183* (2013.01); *A61K 47/34* (2013.01); *C08G 63/64* (2013.01); *C08G 64/18* (2013.01); *C08G 64/406* (2013.01); *C08G 81/00* (2013.01)

(58) Field of Classification Search
CPC ..... C08G 64/183; C08G 64/18; C08G 64/406
See application file for complete search history.

(56) References Cited

U.S. PATENT DOCUMENTS

| 6,201,065 B1 | 3/2001 | Pathak et al. |
| 6,649,702 B1 | 11/2003 | Rapoport et al. |
(Continued)

FOREIGN PATENT DOCUMENTS

| CN | 102614152 A | 8/2012 |
| EP | 1670838 A1 | 6/2006 |

*Primary Examiner* — Michael L Leonard
(74) *Attorney, Agent, or Firm* — Patterson + Sheridan, LLP

(57) ABSTRACT

The present disclosure relates to polythioaminals with applications as carriers or delivery vehicles for therapeutic agents or other small molecule cargo. Polythioaminal block copolymer coupled to a therapeutic agent is a polymer-therapeutic conjugate that exhibits higher stability and longer life time in aqueous environments. The polythioaminal block copolymer coupled to a therapeutic agent can be synthesized by reacting hexahydrotriazines with a hydrophobic block precursor, a hydrophilic block precursor, a particle stabilizing segment precursor, and a cargo, such as a therapeutic agent, in a one pot synthesis. The ease of synthesizing the resulting polythioaminal block copolymer coupled to the therapeutic agent while offering the extended stability and polymer life time in aqueous environments make the polythioaminal block copolymer particularly attractive for therapeutic carriers.

20 Claims, 5 Drawing Sheets

(51) Int. Cl.
  *C08G 64/40*   (2006.01)
  *A61K 47/34*   (2017.01)
  *C08G 81/00*   (2006.01)
  *C08G 63/64*   (2006.01)

(56) References Cited

U.S. PATENT DOCUMENTS

| | | |
|---|---|---|
| 7,879,317 B2 | 2/2011 | Seo et al. |
| 7,884,160 B2 | 2/2011 | Wang et al. |
| 2006/0182788 A1* | 8/2006 | Singh .................. A61K 9/7061 424/448 |
| 2012/0116014 A1* | 5/2012 | Janssen ................ C08G 18/807 524/590 |
| 2014/0335194 A1 | 11/2014 | Lee et al. |
| 2015/0250721 A1 | 9/2015 | Lee et al. |
| 2015/0359777 A1 | 12/2015 | Seo et al. |
| 2015/0366972 A1* | 12/2015 | Boday .................... C08G 12/40 514/772.1 |
| 2017/0065722 A1* | 3/2017 | Boday ................ A61K 49/0002 |

* cited by examiner

PREPARATION OF ROBUST POLYTHIOAMINAL CARRIERS

BACKGROUND

The present disclosure relates, in general, to polythioaminals with applications as carriers or delivery vehicles for therapeutic agents or other small molecule cargo.

Polymer carriers are promising carriers for therapeutic agents in medical applications because polymer composition is highly tailorable, allowing for the capability to tune the polymer's hydrophobic or hydrophilic character, the polymer-therapeutic interaction, the release mechanism and degradability. Despite the numerous advantages, implementation of a polymeric strategy presents its own unique set of challenges. For instance, access to therapeutic-polymer conjugates may require exposure to hazardous organic solvents or reagents, multiple synthetic and/or purification steps, and cytotoxic effects elicited from the resulting polymer (depending on the size).

Furthermore, the life time of the polymer carrier is relatively short in aqueous media. In aqueous solution at room temperature, certain known polymers will degrade over the course of 93 hours, and under physiological conditions (increased temperature and salt content), the polymers degrade much more quickly. While degradation and drug release within this time frame is advantageous for the treatment of certain ailments, other diseases, such as ovarian cancer, require prolonged drug circulation and slow drug release.

Therefore, a stable polymer carrier that is easy to synthesize and couple to therapeutic agents is needed.

SUMMARY

The present disclosure relates, in general, to polythioaminals with applications as carriers or delivery vehicles for therapeutic agents or other small molecule cargo. In one embodiment, a method includes forming a polythioaminal block copolymer by polymerizing a reaction mixture including a hexahydrotriazine, a hydrophobic block precursor, a hydrophilic block precursor, and a particle stabilizing segment precursor.

In another embodiment, a method includes forming a polythioaminal block copolymer particle by polymerizing a reaction mixture including a hexahydrotriazine, a hydrophobic block precursor, a hydrophilic block precursor, and a particle stabilizing segment precursor.

In another embodiment, a polythioaminal block copolymer includes a hydrophobic block joined to a hydrophilic block by a particle stabilizing segment, and the particle stabilizing segment is linked to the hydrophobic block and the hydrophilic block by a thioaminal linkage.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings and in the body of the specification. It is to be noted, however, that the appended and embedded drawings illustrate only typical embodiments of this disclosure and are therefore not to be considered limiting of its scope, for the disclosure may admit to other equally effective embodiments.

Figure 1A:
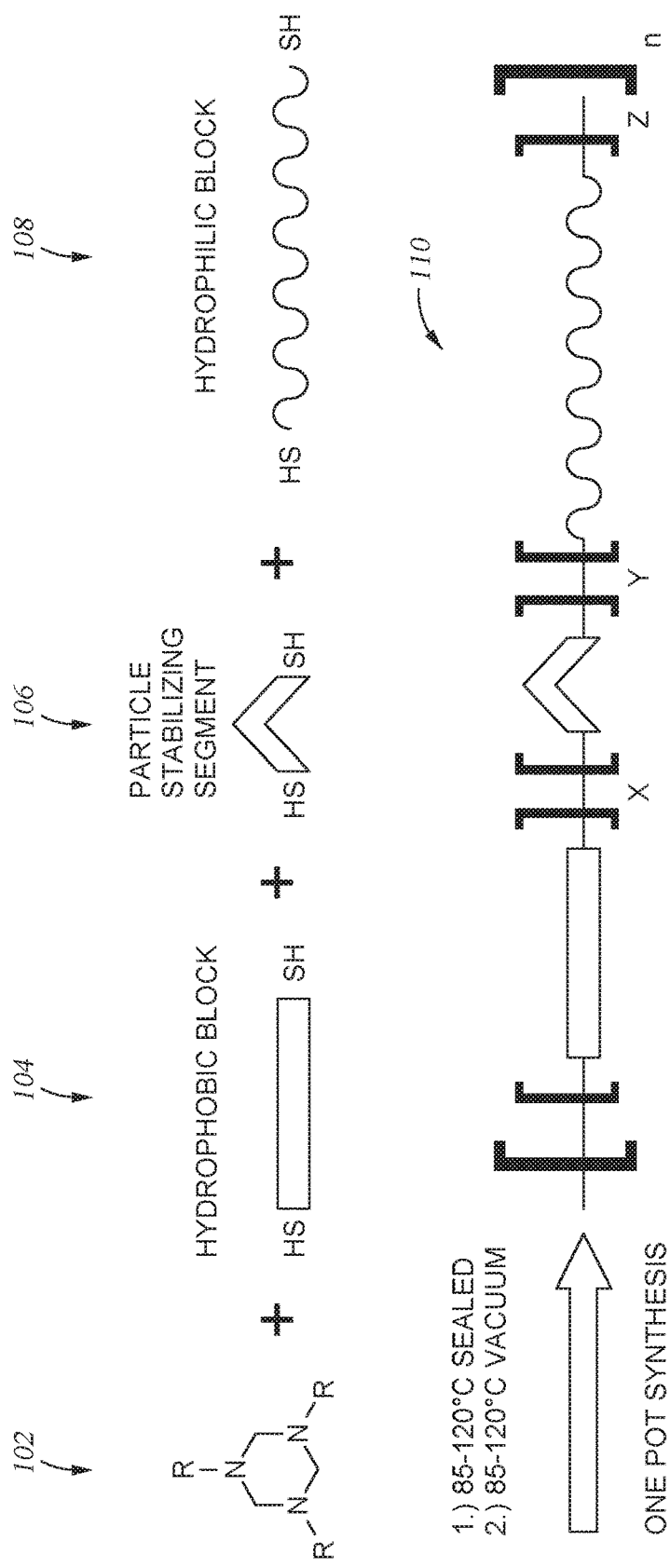
FIGS. 1A-1B depict general schemes for preparing a polythioaminal block copolymer according to embodiments described herein.

To facilitate understanding, identical reference numerals have been used, where possible, to designate identical elements that are common to the figures and drawings. It is contemplated that elements disclosed in one embodiment may be beneficially utilized on other embodiments without specific recitation.

DETAILED DESCRIPTION

The present disclosure relates to polythioaminals with applications as carriers or delivery vehicles for therapeutic agents or other small molecule cargo. A polymer-therapeutic conjugate described herein includes a polythioaminal block copolymer coupled to a therapeutic agent. The polymer-therapeutic conjugates described herein have improved stability and longer life time in aqueous environments. A polythioaminal block copolymer coupled to a therapeutic agent can be synthesized by reacting one or more hexahydrotriazines with a hydrophobic block precursor, a hydrophilic block precursor, a particle stabilizing segment precursor, and a cargo, such as a therapeutic agent, in a one pot synthesis. The polymer thus formed has one or more hydrophobic blocks, one or more hydrophilic blocks, and one or more particle stabilizing segments, where each hydrophobic block is joined to one or more hydrophilic blocks by a particle stabilizing segment linked to the hydrophilic and hydrophobic blocks by a thioaminal linkage. The ease of synthesizing the resulting polythioaminal block copolymer coupled to the therapeutic agent while offering the extended stability and polymer life time in aqueous environments make the polythioaminal block copolymers described herein particularly attractive for therapeutic carriers.

As described herein, the terms "substituent", "radical", "group", "moiety" and "fragment" may be used interchangeably to indicate a point of attachment to a molecule.

Chemical structures are presented herein using the following general notation:

$$[\text{structure}]_n$$

This notation is intended to define a repeated chemical structure within a larger structure, or molecule. Use of brackets around a chemical structure, with a letter subscript "n" generally indicates that the structure is repeated "n" times. Letters other than "n" may be used, and in each case, the letter subscript stands for a positive integer of at least 3. Unless otherwise noted, there is no theoretical upper limit to the value of the subscript. The notation is intended to refer to all possible polymers, of any feasible size, having the structure. However, kinetic and thermodynamic circumstances of individual chemical reactions, such as viscosity, temperature, and monomer availability may limit the growth of polymers in specific cases.

The chemical structures in this disclosure may denote atomic composition of compounds and relative bonding arrangements of atoms in a chemical compound. Unless specifically stated, the geometric arrangement of atoms shown in the chemical structures is not intended to be an exact depiction of the geometric arrangement of every embodiment, and those skilled in the chemical arts will recognize that compounds may be similar to, or the same as, the illustrated compounds while having different molecular shapes or conformations. For example, the structures denoted herein may show bonds extending in one direction, while embodiments of the same compound may have the same bond extending in a different direction. Additionally, bond lengths and angles, Van der Waals surfaces, isoelectronic surfaces, and the like may vary among instances of the same chemical compound. Additionally, unless otherwise noted, the disclosed structures cover all enantiomers, diastereomers, cis/trans isomers, conformers, rotamers, and topomers of the represented compounds. All reactions described herein are performed at nominal conditions (i.e. room temperature to 50° C.) unless otherwise specified.

FIG. 1A depicts general schemes for preparing a polythioaminal block copolymer 110 according to embodiments described herein. As shown in FIG. 1A, the polythioaminal block copolymer 110 is synthesized by reacting a hexahydrotriazine 102 with a hydrophobic block precursor 104, a particle stabilizing segment precursor 106, and a hydrophilic block precursor 108 in a two-step one pot synthesis. The R group of the hexahydrotriazine 102 may be C1 to C6 linear or branched chain. The hydrophobic block precursor 104 may be any suitable biocompatible hydrophobic compound having one or more thiol groups. In one embodiment, the hydrophobic block precursor 104 includes a main component between two thiol groups, as shown in FIG. 1. The main component of the hydrophobic block precursor 104 may be any suitable biocompatible hydrophobic compound. In one embodiment, the main component of the hydrophobic block precursor 104 is a polylactone, such as polycaprolactone, and the hydrophobic block precursor 104 has the general structure:

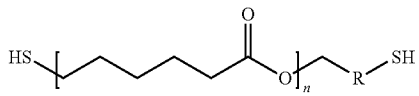

where R is repeating hexanoate units.

In one embodiment, the main component of the hydrophobic block 104 is a polyacrylate, such as poly(methyl acrylate), poly(ethyl acrylate), poly(2-ethylhexyl acrylate), poly(hydroxyethyl methacrylate), poly(butyl acrylate), poly(butyl methacrylate), poly(trimethylolpropane triacrylate), or poly(methyl methacrylate). In one embodiment, the hydrophobic block precursor 104 is poly(methyl methacrylate) having the general structure:

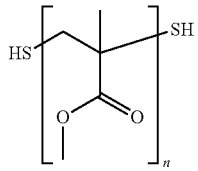

In one embodiment, the main component of the hydrophobic block precursor 104 is polylactic acid, and the hydrophobic block precursor 104 has the general structure:

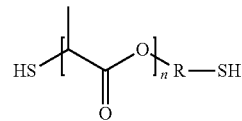

where R is repeating units of lactic acid.

In one embodiment, the main component of the hydrophobic block precursor 104 is poly(trimethylene carbonate), and the hydrophobic block precursor 104 has the general structure:

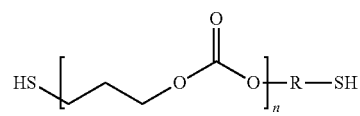

where R is repeating units of propyl carbonate.

In one embodiment, the main component of the hydrophobic block precursor 104 is poly(lactic-co-glycolic acid), and the hydrophobic block precursor 104 has the general structure:

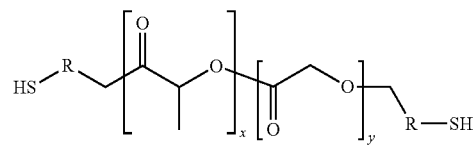

where R is repeating units of lactic acid or glycolic acid, x is the number of units of lactic acid, and y is the number of units of glycolic acid.

In one embodiment, the main component of the hydrophobic block precursor 104 is poly(propylene oxide), and the hydrophobic block precursor 104 has the general structure:

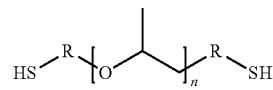

where R is repeating units of propylene oxide.

The particle stabilizing segment precursor 106 may be any suitable biocompatible compound including a main component having hydrogen bonding units and one or more thiol groups attached to the main component. In one embodiment, the particle stabilizing segment precursor 106 includes a main component between two thiol groups, as shown in FIG. 1. The main component of the particle stabilizing segment precursor 106 may be any suitable biocompatible compound having hydrogen bonding units. In one embodiment, the main component of the particle stabilizing segment precursor 106 is polyurea, and the particle stabilizing segment precursor 106 has the general structure:

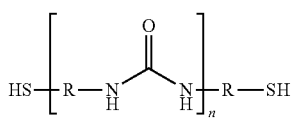

where R is an alkylene group or a hydrophobic group. In one embodiment, the main component of the particle stabilizing segment precursor 106 is polyurethane, and the particle stabilizing segment precursor 106 has the general structure:

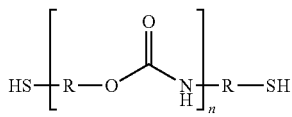

where R is an alkylene group or a hydrophobic group. In one embodiment, the main component of the particle stabilizing segment precursor 106 is polyamide, and the particle stabilizing segment precursor 106 has the general structure:

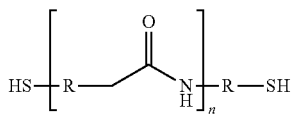

where R is an alkylene group or a hydrophobic group.

The hydrophilic block precursor 108 may be any suitable biocompatible hydrophilic compound having one or more thiol groups. In one embodiment, the hydrophilic block precursor 108 includes a main component between two thiol groups, as shown in FIG. 1. The main component of the hydrophilic block precursor 108 may be any suitable biocompatible hydrophilic compound. In one embodiment, the main component of the hydrophilic block precursor 108 is poly(ethylene glycol), and the hydrophilic block precursor 108 has the general structure:

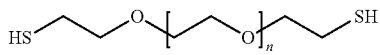

The hexahydrotriazine precursor 102, hydrophobic block precursor 104, particle stabilizing segment precursor 106, and hydrophilic block precursor 108 are reacted to form the polythioaminal block copolymer 110 in a two-step one pot synthesis. The first step is reacting the reactants in a reactor at a temperature ranging from about 85 degrees Celsius to about 120 degrees Celsius to generate oligomers. The reactor may be sealed during the generation of the oligomers. Subsequently, the oligomers are placed under vacuum condition to drive up molecular weight of the product by removing volatile by-products, eventually forming the polythioaminal block copolymer 110, which is the second step of the two-step one pot synthesis. The polythioaminal block copolymer 110, which is a reaction product of the dithiol components, produces block copolymers containing hydrophobic blocks, hydrophilic blocks, and particle stabilizing segments. The polymer blocks in the polythioaminal block copolymer 110 are connected by the sulfur in the thiol group. By using the hexahydrotriazine precursor 102, a polythioaminal block copolymer 110 is formed from the hydrophobic block precursor 104, particle stabilizing segment precursor 106, and hydrophilic block precursor 108. The polythioaminal block copolymer 110 is easy to make and has extended stability and polymer life time in aqueous environments.

Figure 1B:
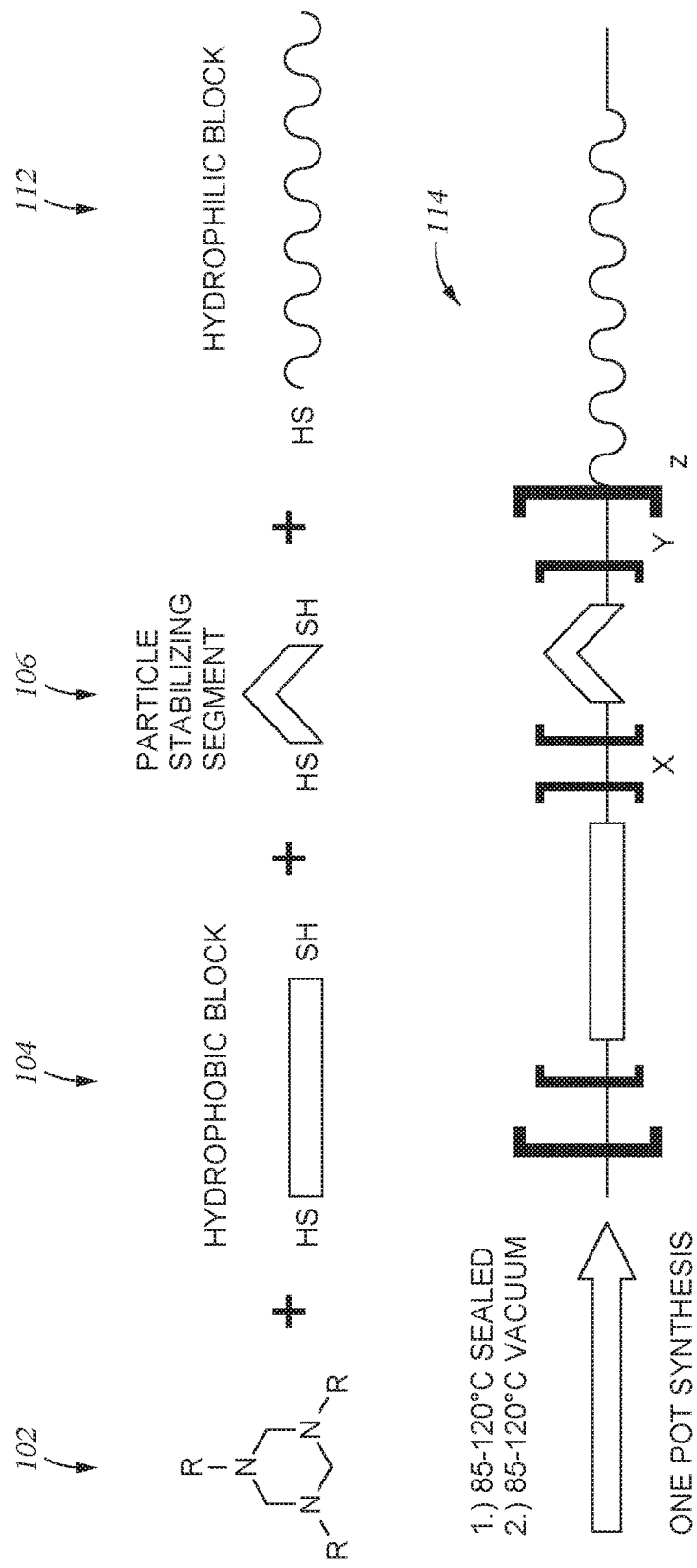
Figure 2:
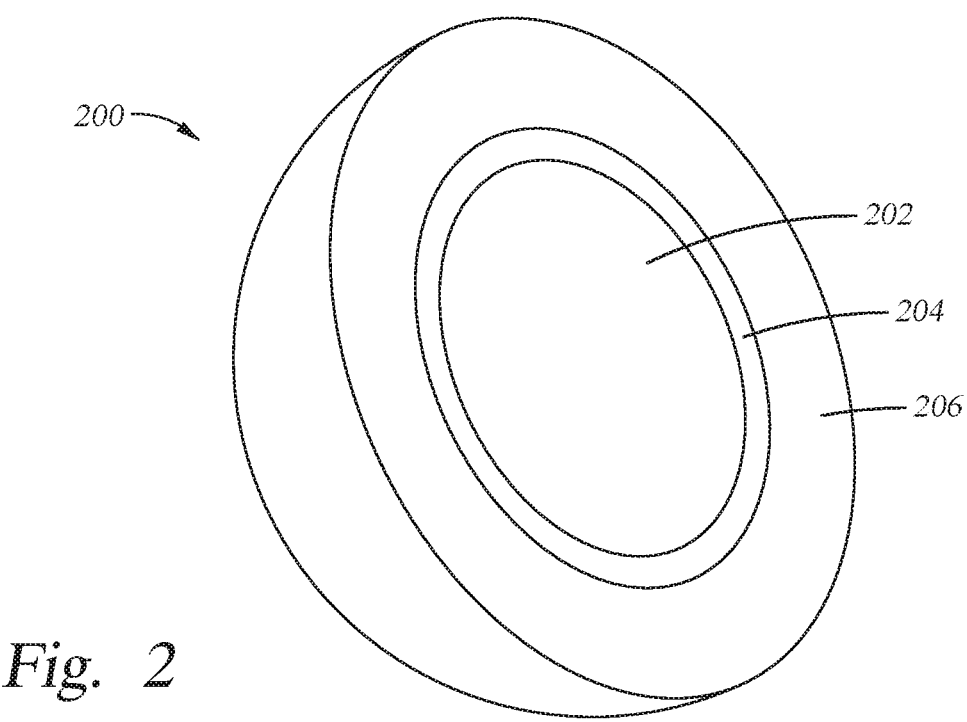
FIG. 2 depicts a polythioaminal block copolymer particle according to embodiments described herein.

In some embodiments, the number of functional thiol groups can be changed to more precisely control the polymer structure. As shown in FIG. 1B, a polythioaminal block copolymer 114 is synthesized by reacting the hexahydrotriazine precursor 102 with the hydrophobic block precursor 104, the particle stabilizing segment precursor 106, and a hydrophilic block precursor 112 in the two-step one pot synthesis previously described. The hydrophilic block precursor 112 may include one thiol group. In one embodiment, the hydrophilic block precursor 112 includes a main component and a thiol group, as shown in FIG. 2. The main component of the hydrophilic block precursor 112 may be any suitable biocompatible hydrophilic compound. In one embodiment, the main component of the hydrophilic block precursor 112 is a polycarbonate, and the hydrophilic block 112 has the general structure:

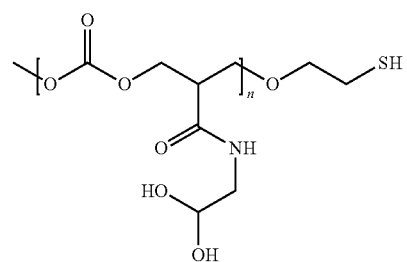

The hydrophilic block precursor 112 may be formed by polymerizing 5-[(2,2-Dihydroxyethylamino)carbonyl]-1,3-dioxan-2-one as shown below:

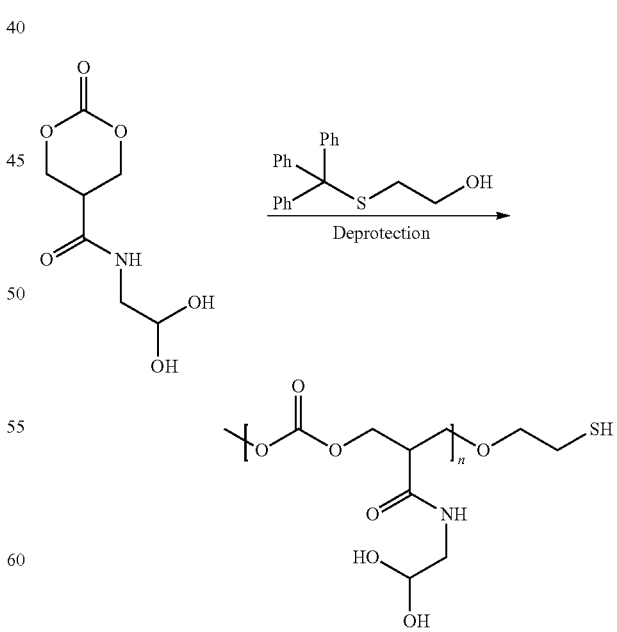

In another embodiment, the main component of the hydrophilic block precursor 112 is a polycarbonate, and the hydrophilic block precursor 112 has the general structure:

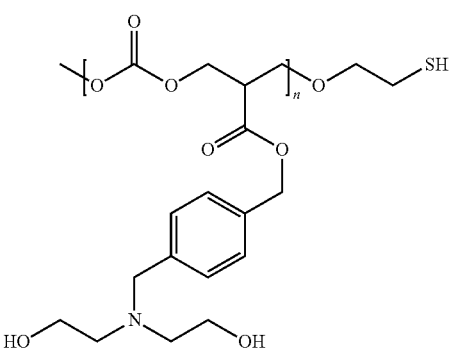

The hydrophilic block precursor 112 may be formed by polymerizing (p-{[Bis(2-hydroxyethyl)amino]methyl}phenyl)methyl 2-oxo-1,3-dioxane-5-carboxylate as shown below:

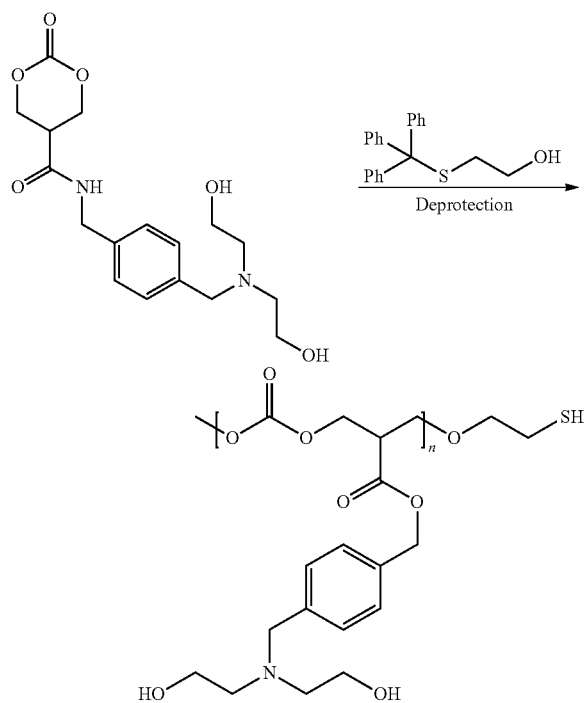

The resulting polythioaminal block copolymer 114 has a different polymer architecture compared to the polythioaminal block copolymer 110 shown in FIG. 1. In some embodiments, the number of functional thiol groups on the hydrophobic block precursor 104 or the particle stabilizing segment precursor 106 may be changed to form polythioaminal block copolymer having different polymer architecture than the polythioaminal block copolymer 110 or 114.

Once synthesized, the polythioaminal block copolymer 110 or 114 can form a particle 200 in aqueous solution, as shown in FIG. 2. The particle 200 may be a micelle, which includes a hydrophobic core 202, a particle stabilizing segment 204 surrounding the hydrophobic core 202, and a hydrophilic shell 206 surrounding the particle stabilizing segment 204. The particle 200 may be a nanoscale (~$10^{-9}$ m) to microscale (~$10^{-6}$ m) particle. In some embodiments, the particle 200 may have a diameter in the range of 20 nm to 200 nm. In this context, diameter refers to a hydrodynamic dimension as measured, for example, by a light scattering method, such as static light scattering (SLS) or dynamic light scattering (DLS), under conditions (e.g., pH, temperature, concentration) corresponding to relevant biological conditions. In a particular embodiment, the volume-weighted average hydrodynamic diameter for a distribution of particles 200 may be in the range of 20 nm to 200 nm for relevant biological environmental conditions.

Figure 3:
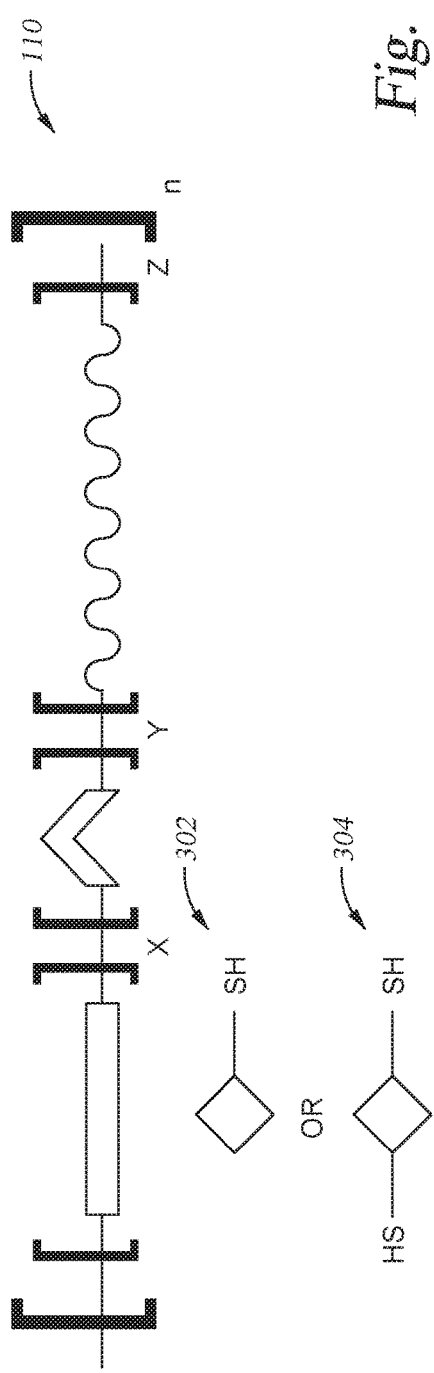
FIG. 3 depicts general schemes for coupling the polythioaminal block copolymer with a cargo according to embodiments described herein.
Figure 3:
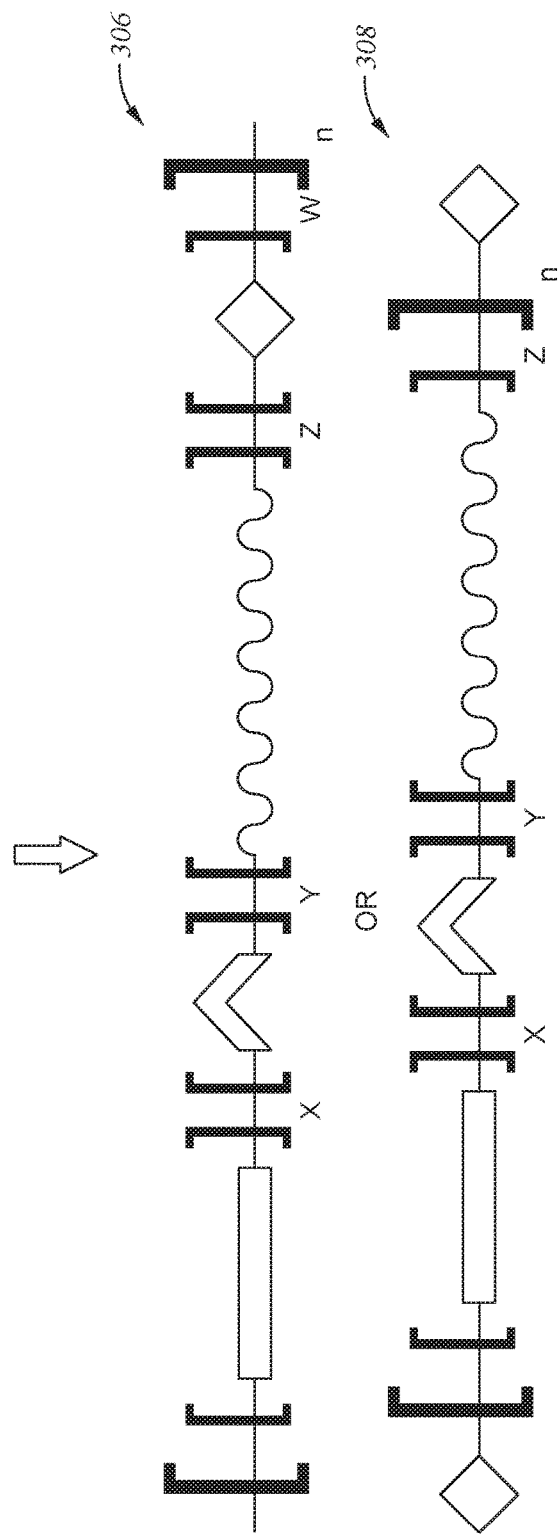

FIG. 3 depicts general schemes for coupling the polythioaminal block copolymer to a cargo according to embodiments described herein. As shown in FIG. 3, a polythioaminal block copolymer, for example the polythioaminal block copolymer 110, can react with a cargo that has one or more thiol groups, such as the cargo 302 or 304, to form a cargo-containing polythioaminal block copolymer 306 or 308. The thiol-terminated cargo 302 or 304 forms a covalent bond with the polythioaminal block copolymer 110. For example, the polythioaminal block copolymer 110 may be first dissolved in a solvent, such as chloroform or methylene chloride. A predetermined amount of cargo 302 or 304 is added to the solution, in which the cargo 302 or 304 is also dissolved. The solution may be stirred for a period of time under nitrogen gas at room temperature. In one embodiment, the period of time is 18 hours. The cargo 302 or 304 may include therapeutic molecules, drug compounds, proteins, DNA fragments, RNA fragments, and/or other molecules or compounds having bioactivity that might be used to treat diseases and/or conditions in a patient.

In one embodiment, the cargo 302 has one functional thiol group, which couples to the polythioaminal block copolymer to form an end-capped polythioaminal block copolymer 308. In another embodiment, the cargo 304 has two functional thiol groups, which couple to other polymer segments to form a cargo-containing polythioaminal block copolymer 306.

Figure 4:
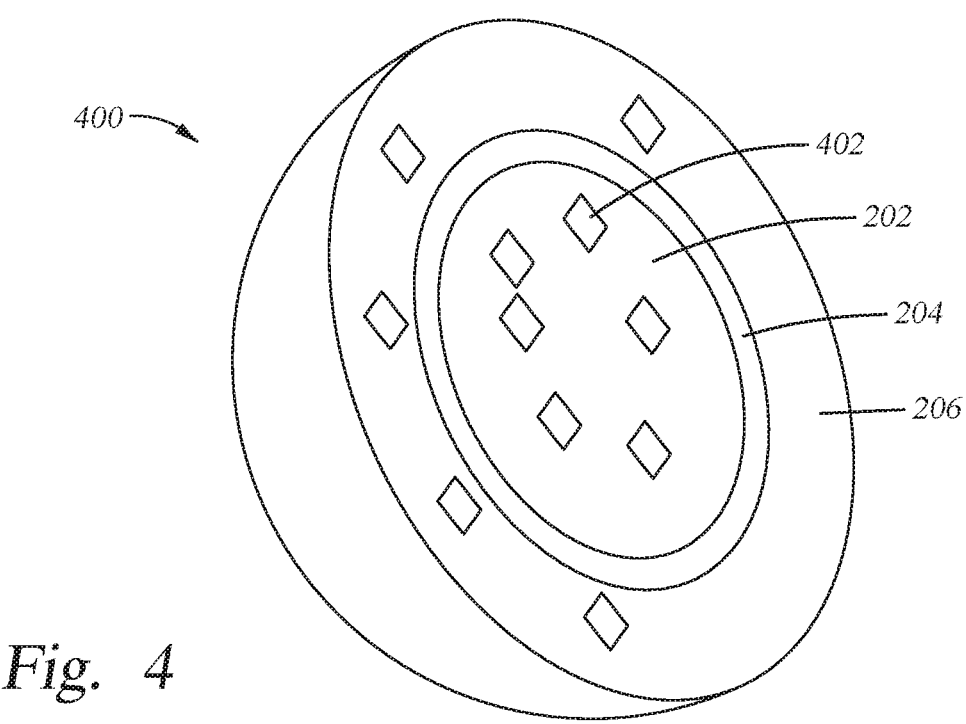
FIG. 4 depicts the polythioaminal block copolymer particle coupled to a cargo according to embodiments described herein.

FIG. 4 depicts the polythioaminal block copolymer particle 200 coupled to a cargo 402 according to embodiments described herein. As described above, the polythioaminal block copolymer 110 or 114 can form the particle 200 in aqueous solution. The polythioaminal block copolymer 110 or 114 can be mixed in aqueous solution with the cargo 402, which in this instance is hydrophobic. When mixed in this manner, the polythioaminal block copolymer 110 or 114 and the cargo 402 aggregate or self-assemble into a particle 400. The particle 400 may also be referred to as a micelle. The cargo 402 may be the cargo 302 or 304 shown in FIG. 3. As shown in FIG. 4, the core of the particle 400 is formed by the hydrophobic core 202. The hydrophobic cargo 402 can be coupled into the hydrophobic core 202 by supramolecular attractions between the hydrophobic components. Cargo coupling capacity of the particle 400 is mainly affected by the interactions between the cargo component(s) and the core 202 of the particle 400. The cargo 402, the hydrophobic core 202, or both may be tailored to adjust load capacity. For example, the length/size of the hydrophobic block precursor 104 (FIG. 1) may be increased or decreased to alter load capacity. The shell of the particle 400 is formed by the hydrophilic shell 206. The hydrophilic shell 206 protects the cargo 402 associated with the hydrophobic core 202 from chemical and biological attack such as enzymatic degradation, opsonization by phagocytes and macrophages, and the like.

It should be noted that dimensions and relative ratios of dimensions for the sub-portions of the particle 400 depicted in FIG. 4 are not necessarily to scale for an actual particle 400. The total number (loading) of the cargo 402 incorporated into the particle 400 is not a limitation and may be any reasonable number greater than or equal to one. It is also possible for the particle 400 to be provided for purposes of storage and/or therapeutic delivery in a mixture with other particles that incorporate no cargo 402. Likewise, when more than one molecule of a cargo 402 is incorporated into a particle 400, it is not a requirement that each such cargo 402 be the same-type of molecule or compound. That is, a mixture of different cargos 402 may be incorporated into a particle such as the particle 400. Similarly, a mixture of several different particles 400 each having a different cargo 402 may be prepared and then administered collectively.

Figure 5:
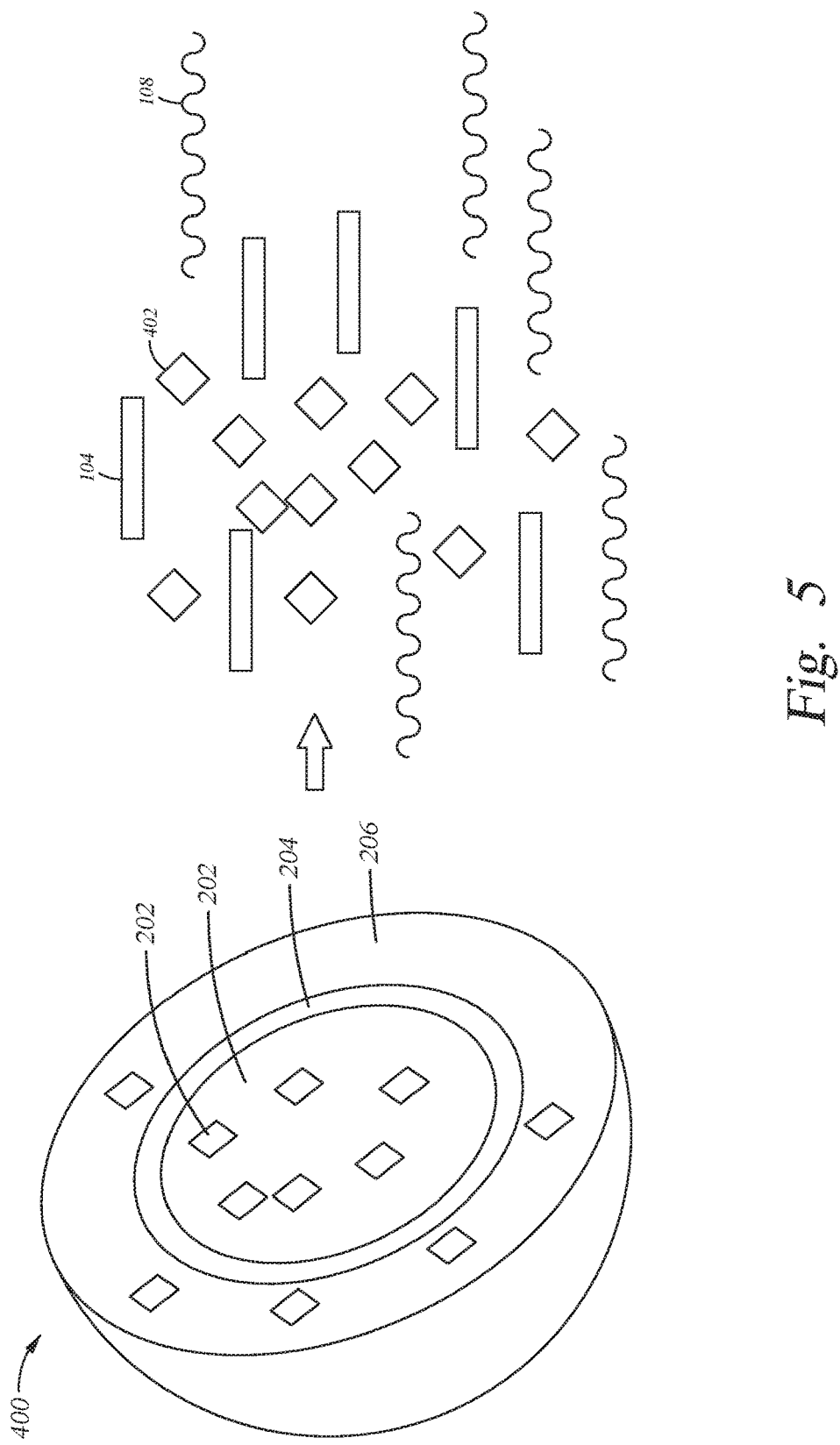
FIG. 5 depicts a triggered cargo release from the polythioaminal block copolymer particle according to embodiments described herein.

FIG. 5 depicts a triggered cargo release from the polythioaminal block copolymer particle 400 according to embodiments described herein. Mechanisms for cargo release at specific target sites generally require destabilization of the particle in one form or another. For instance, the cargo release is triggered by a specific stimulus that is unique to (or at least more prevalent at) the target site. For example, it is known that the extracellular microenvironment of cancerous tissue is often more acidic (pH range about 6.5 to about 6.9) than that of healthy tissue (pH about 7.4). Thus, a cargo release triggered by the pH 6.5 to pH 6.9 range could be used to provide selective cargo release from the particle 400 at a cancerous target site. As shown in FIG. 5, the acidic environment causes the acid sensitive polythioaminal block copolymer particle 400 to depolymerize, breaking the molecules forming the particle 400, releasing the hydrophobic blocks precursor 104, the hydrophilic blocks precursor 108, and the cargo 402.

In another embodiment, the particle 400 undergoes a chemically amplified release, such as placing the particle 400 under oxidation stress. Oxidation of thiols bursts the particle 400 as the hydrophobic core 202 switches to hydrophilic, and complete oxidation also generates the corresponding sulfonic acid, leading to further disruption of the particle 400. Sulfonic acid can lead to quicker degradation of the polythioaminal block copolymer particle 400 since the polythioaminal block copolymer particle 400 is acid sensitive.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
   forming a polythioaminal block copolymer by polymerizing a reaction mixture including a hexahydrotriazine, a hydrophobic block precursor, a hydrophilic block precursor, and a particle stabilizing segment precursor.

2. The method of claim 1, wherein the polythioaminal block copolymer is formed in a two-step one pot synthesis.

3. The method of claim 2, wherein a first step of the two-step one pot synthesis comprises forming oligomers by reacting the hexahydrotriazine, the hydrophobic block precursor, the hydrophilic block precursor, and the particle stabilizing segment precursor in a reactor at a temperature ranging from about 85 degrees Celsius to about 120 degrees Celsius.

4. The method of claim 3, wherein a second step of the two-step one pot synthesis comprises placing the oligomers under vacuum condition to remove volatile byproducts at a temperature ranging from about 85 degrees Celsius to about 120 degrees Celsius.

5. The method of claim 1, wherein the hydrophobic block precursor includes a main component and one or more thiol groups attached to the main component.

6. The method of claim 1, wherein the hydrophilic block precursor includes a main component and one or more thiol groups attached to the main component.

7. The method of claim 1, wherein the particle stabilizing segment precursor includes a main component and one or more thiol groups attached to the main component.

8. A method, comprising:
   forming a polythioaminal block copolymer particle by polymerizing a reaction mixture including hexahydrotriazine, a hydrophobic block precursor, a hydrophilic block precursor, and a particle stabilizing segment precursor.

9. The method of claim 1, wherein the polythioaminal block copolymer particle is formed by forming a polythioaminal block copolymer by polymerizing the reaction mixture and placing the polythioaminal block copolymer in aqueous solution.

10. The method of claim 9, wherein the polythioaminal block copolymer is formed in a two-step one pot synthesis.

11. The method of claim 10, wherein a first step of the two-step one pot synthesis comprises forming oligomers by reacting the hexahydrotriazine, the hydrophobic block precursor, the hydrophilic block precursor, and the particle stabilizing segment precursor in a reactor at a temperature ranging from about 85 degrees Celsius to about 120 degrees Celsius.

12. The method of claim 11, wherein a second step of the two-step one pot synthesis comprises placing the oligomers under vacuum condition to remove volatile byproducts at a temperature ranging from about 85 degrees Celsius to about 120 degrees Celsius.

13. The method of claim 8, wherein the hydrophobic block precursor includes a main component and one or more thiol groups attached to the main component.

14. The method of claim 8, wherein the hydrophilic block precursor includes a main component and one or more thiol groups attached to the main component.

15. The method of claim 8, wherein the particle stabilizing segment precursor includes a main component and one or more thiol groups attached to the main component.

16. A polythioaminal block copolymer, comprising:
    a hydrophobic block joined to a hydrophilic block by a particle stabilizing segment, wherein the particle stabilizing segment is linked to the hydrophobic block and the hydrophilic block by a thioaminal linkage.

17. The polythioaminal block copolymer of claim 16, wherein the hydrophobic block includes a main component, and the main component is a compound selected from the group consisting of: polylactone, polyacrylate, polylactic acid, poly(trimethylene carbonate), poly(lactic-co-glycolic acid), and poly(propylene oxide).

18. The polythioaminal block copolymer of claim 16, wherein the particle stabilizing segment includes a main component, and the main component is a compound selected from the group consisting of: polyurea, polyurethane, and polyamide.

19. The polythioaminal block copolymer of claim 16, wherein the hydrophilic block includes a main component, and the main component is poly(ethylene glycol).

20. The polythioaminal block copolymer of claim 16, wherein the polythioaminal block copolymer is a particle, wherein the hydrophobic block is a hydrophobic core, and the hydrophilic block is a hydrophilic shell, and the particle stabilizing segment is between the hydrophobic core and the hydrophilic shell.

\* \* \* \* \*